US00PP28923P2

(12) United States Plant Patent
Salman

(10) Patent No.: US PP28,923 P2
(45) Date of Patent: Jan. 30, 2018

(54) YELLOW INDIANGRASS PLANT NAMED 'THIN MAN'

(50) Latin Name: *Sorghastrum nutans*
Varietal Denomination: Thin Man

(71) Applicant: David Mark Salman, Santa Fe, NM (US)

(72) Inventor: David Mark Salman, Santa Fe, NM (US)

(73) Assignee: Waterwise Gardening, LLC, Santa Fe, NM (US)

( * ) Notice: Subject to any disclaimer, the term of this patent is extended or adjusted under 35 U.S.C. 154(b) by 21 days.

(21) Appl. No.: 14/999,807

(22) Filed: Jun. 30, 2016

(51) Int. Cl.
*A01H 5/12* (2006.01)

(52) U.S. Cl.
USPC ..... Plt./384

(58) Field of Classification Search
None
See application file for complete search history.

*Primary Examiner* — Susan McCormick Ewoldt

(57) ABSTRACT

'Thin Man' is a new and distinct plant variety of *Sorghastrum nutans*, more commonly known as yellow indiangrass or simply indiangrass. The new variety has blue foliage coloration instead of the more common green coloration; with a growth habit exhibiting an upright and tightly growing vegetation with apical flowering; and exceptional drought and heat tolerance.

2 Drawing Sheets

Figure 1:
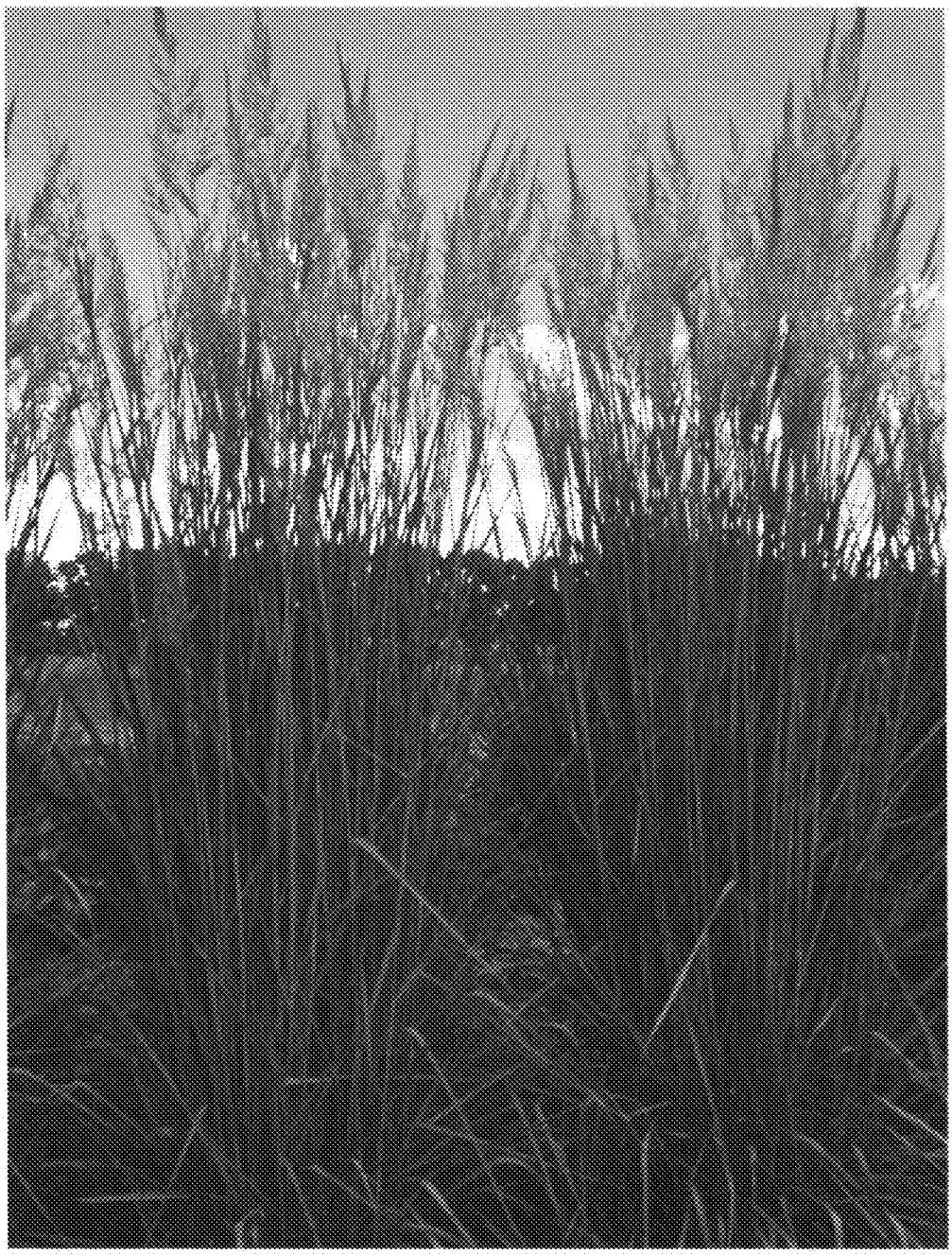

Latin name of the genus and species of the plant claimed: The ornamental plant variety of this invention is botanically identified as *Sorghastrum nutans*.

Variety denomination: The variety denomination is 'Thin Man'.

BACKGROUND OF THE INVENTION

The present invention relates to a new and distinct plant variety of *Sorghastrum nutans*, more commonly known as yellow indiangrass or simply indiangrass. The new variety has blue foliage coloration instead of the more common green coloration; an upright and tightly growing vegetative and flowering growth habit; and exceptional drought and heat tolerance.

Particularly in Southwestern United States, prolonged drought conditions and extended periods of extreme heat temperatures have expanded the commercial market for attractive, drought-tolerant, and vigorous ornamental plants. An important species for habitat, the tall foliage offers cover for birds and small animals and seed heads provide a food source for songbirds and insects.

The original plant of 'Thin Man' was discovered on Aug. 30, 2007 in Los Lunas in Valencia County, N. Mex. in the United States. 'Thin Man' was found in a cultivated field of *Sorghastrum nutans* called 'Llano' (unpatented). 'Llano' was developed from plants of eastern New Mexico provenance primarily for forage and pasture use. These plants were grown for commercial seed production. There were no other plants in the cultivated area. 'Thin Man' is the result of the cross pollination of 'Llano' in this cultivated area and is a chance genetic variation. It was selected for its visibly tighter growth habit and denser foliage than the surrounding grasses.

On the same day of discovery, the plant was transported, divided and replanted into several #5 "gallon" pots and cultivated in a greenhouse located in Santa Fe, N. Mex. The original plants where then transplanted into a trial garden bed in the same nursery where they were observed for approximately 18 months. Propagation via crown division began in the summer of 2009 under the direction of the inventor of the present invention. Field-grown plants were divided in late spring and potted into nursery pots. Testing was repeated in professional nursery settings in Santa Fe, N. Mex. and Fort Collins, Colo. Propagation testing continued through three generations and testing demonstrated the distinct characteristics described herein. These characteristics are true-to-type and transmissible by asexual reproduction with uniformity and stability.

BRIEF SUMMARY OF THE INVENTION

The following traits represent the characteristics of the new variety 'Thin Man'. These traits in combination distinguish this variety from all other commercial varieties known to the inventor.

1. Blue foliage coloration;
2. Habit displaying an upright, tightly growing vegetation with apical flowering growth;
3. Exceptional drought tolerance; and
4. Exceptional heat tolerance.

Plant Breeder's Rights for this variety have not been applied for and 'Thin Man' has not been offered for sale more than a year before the filing date of this application. 'Thin Man' has not been promoted under any other breeder's reference or cultivar name.

Plants of 'Thin Man' have not been observed under all possible environmental and cultural conditions. The phenotype may vary somewhat with variations in environmental conditions, for example, with fluctuation in temperature, soil chemistry, and photoperiod without, however, any variance in genotype.

BRIEF DESCRIPTION OF THE PHOTOGRAPH(S)

The accompanying colored photographs illustrate the overall, typical appearance of the new and distinct yellow indiangrass plant showing the colors as true as it is reasonably possible to obtain in colored reproductions of conventional photography. Due to color variation reproduced in the photographs, color characteristics of this new variety should be determined with reference to the observations described herein, rather than a reliance on the photographs alone. Photographs were taken outdoors on Sep. 1, 2015 of a three-year-old plant. The different photographs are intended to represent the distinctive characteristics of 'Thin Man'.

FIG. 1, demonstrates growth habit and overall appearance of the invention.

Figure 2:
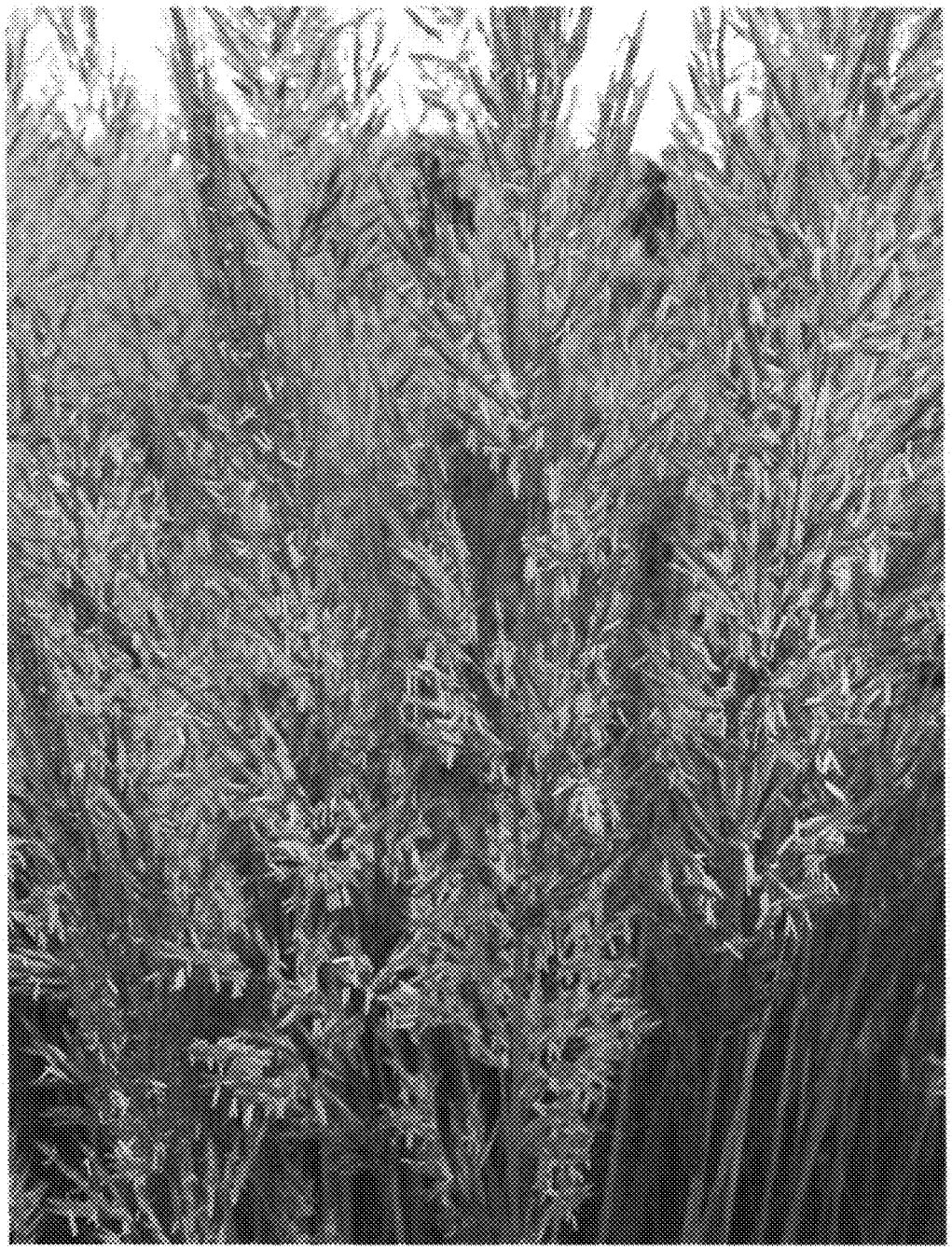

FIG. 2 is a close up view of the flower spikes and leaves of the same plant.

DETAILED BOTANICAL DESCRIPTION

The following is a detailed description of the new variety 'Thin Man'. Characteristic data was collected in the Fall of 2016. The color determinations are in accordance with the 2007 edition of The Royal Horticultural Society Colour Chart published by The Royal Horticultural Society (London, England), except where general color terms of ordinary dictionary significance are used and color readings were observed under natural, outdoor light.

VARIETY DESCRIPTION

Classification:

*Botanical.*—*Sorghastrum nutans.*

*Common.*—Yellow Indiangrass.

Parentage:

*Female.*—An improved pasture selection of *Sorghastrum nutans* 'Llano' (unpatented).

*Male.*—*Sorghastrum nutans* 'Llano' (unpatented).

Propagation: Crown divisions.

Plant:

*Type.*—Herbaceous perennial grass.

*Ploidy.*—Diploid.

*Growth habit.*—Dense upright tuft with flowering spikes held upright above the foliage.

*Height, unpruned* (*average*) (*m*).—1.4 m.

*Spread* (*average*) (*cm*).—46 to 60 cm.

*Root description.*—Fibrous and fine, deeply rooted. Root color: RHS 199A to 199C.

*Life cycle duration.*—Perennial.

*Cold tolerance.*—USDA 4 to 8.

*Optimal temperature range.*—Very tolerant of a wide range of growing temperatures including triple digit summer heat and subzero winter cold.

Culm (stem): Cylindrical, hollow pith, thin but strong, and erect.

*Number* (*average*).—40, forming a tight clump.

*Size* (*average*).—3.0 mm in diameter and 90.0 cm in height (from the base to the base of the peduncle).

*Surface.*—Glabrous, smooth, and lightly striate and glaucescent near nodes.

*Color* (*during summer and fall*).—RHS182A to 182C and lightly suffused with 150D (sun exposed portion of culm) and RHS150D (shade side).

*Internode.*—Length (average) (cm): 27.0 cm.

Leaf:

*Leaves per culm* (*average*).—3 on flowering culms.

*Leaf shape.*—Narrowly lanceolate.

*Leaf division.*—Simple.

*Leaf margin.*—Entire, scaberulose.

*Leaf base.*—Sheathed to base of the node.

*Leaf venation.*—Parallel, not distinguishable in color from leaf coloration.

*Leaf width.*—An average of 8.0 mm at widest section.

*Leaf length* (*average*) (*cm*).—Blade: 35.0 cm. Sheathed portion: 18.0 cm.

*Leaf color.*—Blend between RHS 138A and 139B (upper and lower surfaces).

*Ligule.*—Hairy type with fine hairs. Height (average) (mm): 2.5 mm. Width (average) (mm): 4.0 mm en masse. Color: RHS 155B.

Inflorescence: Slender, upright, freely branched panicle at terminus of stem, with paired spikelets.

*Blooming period.*—Late summer to fall (as observed in Santa Fe, N. Mex., United States located at 35.6870° N, 105.9378° W).

*Number.*—One per culm.

*Size* (*average*) (*cm*).—Length (cm): 25.0 cm. Width (cm): 3.0 cm.

*Color.*—Panicles en masse RHS 161A to 161B.

*Spikes.*—Number (average): 200 per panicle. Shape: Elliptic. Length (average) (mm): 7.0 mm. Width (average) (mm): 1.5 mm.

*Awn.*—Present. Length (average) (cm): 1.7 cm. Color: Bend between RHS 161A and 175B.

*Lemma.*—Shape: Elliptic. Apex: Acute. Truncate base: Glabrous, smooth, glossy surface. Length (average) (mm): 6.0 mm. Width (average) (mm): 1.0 mm. Color: RHS 165B to 165C.

*Glumes.*—Symmetrical and feather-like with many thread-like hairs feathering out from a central axis. Shape: Elliptic. Surface: Translucent and glossy. Length (average) (mm): 6.0 mm. Width (average) (mm): 0.7 mm. Color: RHS NN155D.

*Rachis.*—Length (average) (cm): 40.0 cm (from last leaf). Panicle portion: Length (average) (cm): 24.0 cm. Width (average) (mm): 1.2 mm. Surface: Glabrous, smooth. Color: Blend between RHS158A and 181D. Lateral branches: Peduncle-like. Number (average): 5 bunches of 4 peduncle-like branches spaced evenly along the rachis. Surface: Glabrous, smooth. Length (average) (cm): 5.5 cm (shortest at the terminus). Width (average) (mm): 0.2 mm. Color: Blend between 161C and 181B.

*Pedicel.*—Very fine and wiry. Surface: Glabrous, smooth. Length (average) (mm): 5.0 mm. Width (average) (mm): 0.1 mm. Color: RHS 161C to 161D.

Reproductive organs:

*Androecium.*—Stamen Number: 3. Length (average) (mm): 4.5 mm. Width (average) (mm): 0.3 mm. Anthers: Basifixed on very fine, translucent filaments. Color: RHS 155A. Pollen: Not present.

*Gynoecium.*—Pistil: 1 to 2 plumose stigmas on short fine styles. Length (average) (mm): 1.5 mm. Width (average) (mm): 0.5 mm. Color: RHS NN155B. Ovary: Unilocular, superior. Shape: Oval. Length (average) (mm): 1.0 mm. Width (average) (mm): 0.5 mm. Color: RHS 163C.

Best mode growing conditions:

*Soil conditions.*—Grows well in clay, loam, silt, silt-loam soil conditions.

*Water use/drought tolerance.*—Drought tolerant when planted in the ground.

*Fertilization.*—Propagation: Use standard water soluble 15-15-15 or similar formulation every week to two weeks during growing season. Landscape cultivation: Top dressing of garden/landscape plants in fall with a blend of compost and good quality natural/organic fertilizer.

COMPARISON TO SIMILAR VARIETIES

In comparison to Parents (both unpatented), 'Thin Man' has a visibly tighter growth habit and denser foliage.

In comparison to the commercially available variety of *Sorghastrum nutans* named 'Indian Steel' (unpatented), 'Thin Man' is slightly taller; and its mature form is more uniform, both in height and width; the blue foliage coloration is more uniform in 'Thin Man'. The genetics in 'Thin Man' are more xeric and heat tolerant due to its origination in the western United States climate. Further, 'Thin Man' is propagated by crown division, whereas, 'Indian Steel' is propagated via seed.

The comparison variety to 'Thin Man' is the commercially available variety of *Sorghastrum nutans* named 'Sioux Blue' (unpatented), which was introduced by Longwood Gardens, Kennet Square, Pa. and was selected as a seedling of variety 'Osage'. The growth habit of the stems and foliage are more upright for 'Thin Man'. The genetics in 'Thin Man' are more xeric and heat tolerant due to its origination in the western United States climate of eastern New Mexico, which is drier and hotter than where variety 'Osage' originated in Oklahoma and Kansas.

'Thin Man' differs from the commercially available *Sorghastrum nutans* named 'Cheyenne' in that 'Thin Man' has very blue foliage compared to the green foliage of 'Cheyenne', is more uniform in mature size (both height and width), and is propagated by crown divisions, not via seed as is the case of 'Cheyenne'.

I claim:

1. A new and distinct variety of yellow indiangrass as described and illustrated herein.

* * * * *